(12) United States Patent
O'Connell et al.

(10) Patent No.: US 8,790,586 B2
(45) Date of Patent: Jul. 29, 2014

(54) MOLECULAR EXCHANGE DEVICE

(75) Inventors: Mark Thomas O'Connell, Huntingdon (GB); Stewart Jeffrey Block, London (GB)

(73) Assignee: Probe Scientific Limited, London (GB)

( * ) Notice: Subject to any disclaimer, the term of this patent is extended or adjusted under 35 U.S.C. 154(b) by 1007 days.

(21) Appl. No.: 12/443,449

(22) PCT Filed: Sep. 28, 2007

(86) PCT No.: PCT/GB2007/003695
§ 371 (c)(1),
(2), (4) Date: Jul. 27, 2009

(87) PCT Pub. No.: WO2008/038015
PCT Pub. Date: Apr. 3, 2008

(65) Prior Publication Data
US 2010/0016779 A1    Jan. 21, 2010

(30) Foreign Application Priority Data
Sep. 28, 2006   (GB) .................................. 0619157.1

(51) Int. Cl.
*A61M 25/00*   (2006.01)
*B29C 35/08*   (2006.01)
*B44C 1/22*    (2006.01)

(52) U.S. Cl.
USPC ........... 422/255; 600/581; 600/585; 600/366; 600/309; 604/6.16; 604/29; 604/27; 604/43; 604/48; 604/93.01; 604/174; 604/264; 604/523; 604/524; 604/525; 210/321.64; 210/321.71; 210/321.79; 210/321.8; 210/321.87; 210/321.88; 210/321.89; 210/500.21; 210/500.23; 73/61.41

(58) Field of Classification Search
None
See application file for complete search history.

(56) References Cited

U.S. PATENT DOCUMENTS

| 3,670,772 A | 6/1972 | Ziemek et al. |
| 3,981,299 A | 9/1976 | Murray |
| 4,265,249 A | 5/1981 | Schindler et al. |
| 4,694,832 A | 9/1987 | Ungerstedt |
| 4,707,268 A | 11/1987 | Shah et al. |

(Continued)

FOREIGN PATENT DOCUMENTS

| EP | 0381062 A2 | 8/1990 |
| EP | 0558071 A  | 9/1993 |

(Continued)

OTHER PUBLICATIONS

International Search Report for International Application No. PCT/GB2007/003695, (May 26, 2008) (7 pages).

(Continued)

*Primary Examiner* — Jill Warden
*Assistant Examiner* — Timothy G Kingan
(74) *Attorney, Agent, or Firm* — Klarquist Sparkman, LLP

(57) ABSTRACT

The present application relates to a molecular exchange device (1) for use with an analysis and control apparatus and a method of manufacturing a molecular exchange device. The molecular exchange device comprises a casing (2), extending from a proximal end (3) to a distal end (4), supporting at least two fluid passageways (7a, 7b) extending from the proximal end to the distal end; the casing comprising at least one exchange aperture (9a, 9b) between the distal end and the proximal end, wherein a portion of the fluid passageway exposed by the exchange aperture is porous

41 Claims, 5 Drawing Sheets

(56) References Cited

U.S. PATENT DOCUMENTS

| | | | |
|---|---|---|---|
| 5,106,365 A | | 4/1992 | Hernandez |
| 5,156,844 A | * | 10/1992 | Aebischer et al. ............ 424/424 |
| 5,191,900 A | * | 3/1993 | Mishra ......................... 600/585 |
| 5,441,481 A | * | 8/1995 | Mishra et al. ................... 604/29 |
| 6,299,593 B1 | | 10/2001 | Wakabayashi |
| 6,346,090 B1 | | 2/2002 | Liska et al. |
| 6,478,767 B1 | | 11/2002 | O'Connell |
| 6,616,625 B2 | | 9/2003 | Hindl |
| 6,805,683 B1 | | 10/2004 | Johansson |
| 6,929,618 B1 | * | 8/2005 | Johansson ................... 604/6.16 |
| 2003/0060751 A1 | | 3/2003 | Haindl |
| 2003/0236454 A1 | | 12/2003 | Liska et al. |
| 2005/0119588 A1 | | 6/2005 | Model et al. |
| 2005/0251087 A1 | | 11/2005 | Carr et al. |
| 2005/0277820 A1 | | 12/2005 | Wright et al. |
| 2006/0079830 A1 | * | 4/2006 | Putz ................................ 604/28 |
| 2007/0095756 A1 | | 5/2007 | Hardwicke et al. |

FOREIGN PATENT DOCUMENTS

| | | |
|---|---|---|
| EP | 0732973 A1 | 4/1995 |
| EP | 0675695 B1 | 10/1995 |
| EP | 1101501 A1 | 5/2001 |
| EP | 1105045 B1 | 6/2001 |
| FR | 2655548 A1 | 6/1991 |
| GB | 2030454 A | 4/1980 |
| GB | 2053719 A | 2/1981 |
| GB | 2130916 A | 6/1984 |
| JP | 61 206459 A | 9/1986 |
| JP | 61206459 A | 9/1986 |
| WO | WO 93/00128 A | 1/1993 |
| WO | WO 98/46339 | 10/1998 |
| WO | WO 01/03763 A | 1/2001 |
| WO | WO 01/06928 A1 | 2/2001 |
| WO | WO 01/19444 A1 | 3/2001 |
| WO | WO 2004/033000 A1 | 4/2004 |

OTHER PUBLICATIONS

UK Intellectual Property Office Search Report for Application No. GB0619157.1 (Jun. 20, 2007) (4 pages).

Written Opinion for International Application No. PCT/GB2007/003695 (May 26, 2008) (8 pages).

United Kingdom Intellectual Property Office, United Kingdom Search Report for Great Britain Application No. GB0802667.6, Jun. 13, 2008, 4 pages.

International Search Report and Written Opinion of the International Searching Authority, mailed May 7, 2009, for International Application No. PCT/GB2009/000321, 12 pages.

United Kingdom Intellectual Property Office, United Kingdom Search Report for Great Britain Application No. GB0802669.2, Jun. 13, 2008, 4 pages.

International Preliminary Report on Patentability and Written Opinion of the International Searching Authority, mailed Mar. 31, 2009, for International Application No. PCT/GB2007/003695, 9 pages.

International Search Report and Written Opinion of the International Searching Authority, mailed Dec. 8, 2010, for corresponding International Application No. PCT/GB2009/000312, 13 pages.

International Search report for PCT Application No. PCT/GB2007/003695; 6 pp., (May 26, 2008).

* cited by examiner

MOLECULAR EXCHANGE DEVICE

CROSS REFERENCE TO RELATED APPLICATIONS

This is the U.S. National Stage of PCT Application No. PCT/GB2007/003695, filed Sep. 28, 2007, which was published in English under PCT Article 21 (2), which in turn claims the benefit of Great Britain Application No. GB 0619157.1, filed Sep. 28, 2006.

DESCRIPTION OF INVENTION

The present invention relates to a molecular exchange device. In particular, the present invention relates to a molecular exchange device for use with an analysis and control apparatus and a method of manufacturing a molecular exchange device.

Molecular exchange devices, such as dialysis probes, are known in the art. Such probes relate to use for insertion into a subject, such as in a blood vessel, for use in dialysis, detection of substances or levels of substances within the subject. Such probes generally include a porous membrane past which a perfusion fluid is supplied and removed. Molecules from the perfusion fluid can pass through the membrane into the subject and vice versa. In the latter case, analysis can be carried out using internal or external apparatus to ascertain the presence of certain molecules and their concentrations.

The membranes used for dialysis tubing such as that in the prior art probes typically have very thin walls to promote effective diffusion, which means that they provide very little structural support and, as such, the thin walls do not maintain their shape in use. In order to provide additional support to the membranes, the first probes had a thin wire placed within the centre of the tubing to provide support for the membranes during insertion into the subject, as well as to prevent the walls of the membrane from collapsing when the membrane is bent.

However, despite that addition of a thin wire, such probes are still prone to collapsing against the metal wire during insertion and, particularly, when bent. In an attempt to overcome this problem, the wire was replaced by a hollow tube within the membrane, typically positioned along the longitudinal axis of the probe. The hollow tube provides elongated support that also acts as a supply or a return line for the perfusion fluid.

One of the major disadvantages of using such forms of internal support for the membrane was damage to the membrane during the insertion of the internal support and during insertion into a subject.

In a further attempt to overcome the problem of providing sufficient support to the membrane, probes were formed having short lengths of membrane tubing glued on to a supporting structure such as a hollow stainless steel tube. The steel tube provides elongation and assists in the insertion of the device. The disadvantage with such probes is that, under physiological conditions, the glue used in the assembly of such probes weaken due to contact with fluids, resulting in fragmentation of the membrane tubing from the supporting structure within the subject. The membrane tubing of such hollow tubes could also fragment due to mechanical damage caused during insertion into the subject.

In view of the use of such probes within a subject (i.e. a human or animal body), it is clear that fragmentation of the membrane is not desired due to the potential damage that could be caused. When this occurs in tissue such as muscle it is unfortunate but, as the materials of the membrane are relatively bio-compatible, this is not disastrous. However, when this occurs in a system within a subject such as the circulatory system, lost fragments could be moved into areas (for example the heart) where they could be life threatening. Even if such fragments are spotted before serious damage can occur, the removal of such fragments causes further injury.

EP 0675695 discloses a dialysis probe wherein the dialysis membrane is attached at the proximal end of the probe to overcome the possibility of the probe becoming loose from its anchor, due to the fact that the anchoring area is not within the subject. Although reasonably effective, this is a relatively complicated and expensive probe to manufacture. Moreover, the tip is not protected in any way, which leaves it vulnerable to damage.

In an attempt to overcome the disadvantages described above, EP-A-1105045 discloses an arrangement in which a tube formed of a dialysis membrane is mounted on a relatively stiff support member. In particular, the support member is elongate and a tubular dialysis membrane extends along one longitudinal side, folds back in a U shaped fashion, through an eye or a notch, at the distal end of the support member, and then passes back against the opposite longitudinal side. The support member provides support for the tubular membrane and as such, the probe is more robust and cost effective than its predecessors.

However, the support member does not provide any protection to the external walls of the membrane. In particular, there are no means provided to maintain the walls of the membrane in position during use, to ensure that flow of fluid within the tubular membrane is not impeded. Furthermore, the folding of the membrane in the U shaped fashion may cause a kink and/or creases in the membrane at the tip of the probe, which can impede the flow of a fluid within the tubular membrane and, consequently, impedes the efficiency and accuracy of the probe. Moreover, this probe is still relatively complex and, due to the complexity of the manufacturing process, costly to manufacture. Without pre-treating the tubular membrane it is difficult to insert the membrane around the support member, thereby necessitating further complexity to the manufacturing process. Furthermore, maintaining the tubular membrane in position against the support has been found to be difficult.

WO 99/45982 discloses a catheter for insertion into a blood vessel for detecting substances. The catheter disclosed therein comprises an elongate body that includes two channels through which the microdialysis solution can flow. An opening is defined in the catheter body. A microdialysis membrane, which is attached to the outside of the catheter body, covers the opening across which membrane microdialysis may take place. The bonding of the dialysis membrane to the outside of the probe body, means that there is a high risk that the microdialysis membrane will fragment from the catheter body, which results in the disadvantages discussed above with regard to fragmentation.

U.S. Pat. No. 7,008,398 discloses a micro-dialysis probe in which dialysis can occur along the entire length of the dialysis membrane. The only protection provided by the walls of the probe reduces the overall surface area of the dialysis membrane and thus the efficiency of the dialysis across the membrane.

US 2005/0251087 discloses a microdialysis probe that is supported by an elongated external frame to hold the tubular membrane in a desired configuration. However, the tubular membrane is not held securely by the frame and there is a great risk that the fragile construction could easily break during use. Furthermore, little protection is provided for the tubular membrane in this arrangement, which could lead to the disconfiguration of or damage to the tubular membrane when inserted into a subject. Moreover, a great deal of material is required to form a frame of sufficient strength and, as such, increases the size of the overall device with respect to the volume of fluid that can be passed through the device, which makes it both more invasive when inserted into the subject and more expensive to produce.

It is an object of the present invention to provide a molecular exchange device that overcomes or mitigates some or all of the above disadvantages.

For the avoidance of doubt, the following terms are intended to have the definitions as outlined below:

Molecular exchange is the selective exchange of any suitable molecule or composition, including but not limited to dialysis, ultra filtration, drug delivery etc., from the device to the external environment and vice versa.

The casing is constructed from any suitable material, such that the substantial flow of fluid or molecules is prevented through its walls in the environment within which it is intended to be used. Hence, in biological applications where the molecular exchange device is intended to be inserted in a human or animal body, the casing is made of a material that is resistant to a biological biocompatible environment and prevents substances from penetrating through the casing. The material of the casing must also be rigid enough to ensure the device is not easily damaged during insertion, but flexible enough to allow a degree of bending of the device during use. Preferably, the casing is constructed from high density polyethylene (HDPE), polyamide, carbon fibre, stainless steel or similar material.

The distal end of the casing is the end of the device that is intended to be inserted into the environment in which molecular exchange is desired.

The proximal end of the casing is the end of the device that is not intended to be inserted into the environment in which molecular exchange is desired. The distal and proximal ends of the casing are adapted to allow the insertion/withdrawal of perfusion fluid to/from the fluid passageways.

The distal and proximal ends are also adapted to allow insertion/withdrawal of additional components, such as probes, sensors, connectors to monitoring/analysing systems etc.

The at least one exchange aperture is a portion of the casing that exposes the adjacent portion of the fluid passageway. The exchange aperture may be an opening in the external wall of the cavity. Alternatively, the exchange aperture may be a porous area that permits the exchange of selected molecules to/from the fluid passageways from/to the environment external to the device.

The porous portions are porous to the extent that they permit the selective exchange of molecules across the fluid passageway and/or casing. A skilled person would appreciate that different sized molecules will require different porosities to permit the selective exchange of molecules.

A flow chamber provides the passage of fluid from at least one fluid passageway to another at least one fluid cavity. For example, the flow chamber may provide passage of fluid from one fluid passage way to another fluid passageway through, for example, a connecting tube or an open chamber.

The subject is any suitable environment in which the device may be applied. For example, the subject can be a human or animal body. Alternatively, the subject could be part of a industrial, chemical or fermentation process.

In a first aspect of the present invention there is provided a molecular exchange device comprising a casing, extending from a proximal end to a distal end, supporting at least two fluid passageways extending from the proximal end to the distal end; the casing comprising at least one exchange aperture between the distal end and the proximal end, wherein a portion of the fluid passageway exposed by the exchange aperture is porous.

The main advantage provided by the molecular exchange device in accordance with the present invention is that the casing supports and protects the at least two fluid passageways. The casing further ensures that the porous portion of the passageway will not fragment in use, whilst ensuring that the passageway maintains its shape and maximises the flow of fluid therein.

In an advantageous embodiment of the present invention, a separator extends along the casing for at least the length of the exchange aperture, separating the at least two fluid passageways. In a further advantageous embodiment, the separator extends along substantially the entire length of the casing, from the distal end to the proximal end, separating the at least two fluid passageways. Preferably, the separator extends along the central axis of the casing. The separator provides the advantage of ensuring that there is no exchange of fluid between two or more fluid passageways, thereby improving dialysis efficiency. The separator also provides support to the two or more fluid passageways, particularly at the porous portion of the passageway. The separator may or may not be integral with the casing.

Advantageously, the two fluid passageways may be arranged on aligning sides of the central separator. Advantageously, two or more fluid passageways may be arranged around the central separator. Preferably pairs of fluid passageways in fluid communication with one another may be arranged around the central separator to permit multiple sets of molecular exchange in one device. The molecular exchange may be for analysis, dialysis, delivery, recovery and extraction of substances etc. During use in a subject, for example, one set of fluid passageways may deliver a drug to the external environment of the device, whereas another set of fluid passageway may be used for recovery, extraction or analysis of a substance from the environment surrounding the device into the passageway to measure the overall drug content. It is envisaged that each set of fluid passageways will be selected for a particular function.

In an advantageous embodiment the at least two fluid passageways are at least partially defined by the casing and/or separator. Alternatively, the at least two fluid passageways are not at least partially defined by the casing and/or separator. For example, the fluid passageways are at least one tube held within the casing. In one embodiment of the invention the porous region of the fluid passage way is a porous membrane bonded within the casing at the proximal and distal ends of the exchange aperture. Preferably, the at least one tube is a porous membrane. More preferably, the porous membrane is a dialysis membrane.

In an embodiment of the invention, substantially the entire area of the tube is porous. In this embodiment, the tube can be made of a single type of material, which obviates the need for forming a separate porous portion in the conduit adjacent to the exchange aperture and makes the molecular exchange device even cheaper to manufacture. This embodiment also provides the advantage that the porous portion does not need to be carefully aligned with the at least one exchange aperture of the casing. As the hollow tube is only exposed to the external environment at the exchange aperture of the casing, molecular exchange will only occur at these desired points of the casing.

In a preferred embodiment the at least one tube extends from the proximal end to the distal end of the casing, folds back on itself at the distal end and extends from the distal end to the proximal end of the casing, providing two fluid passageways.

Advantageously, the at least one tube has a circular or non-circular shaped cross section. This enables the hollow tube to be positioned in the correct orientation within the casing. For example, the cross section may have one or more straight edges or be D-shaped or be profiled to orientate the hollow tube in such a way as to optimise its efficiency for exchange.

In preferred embodiments the fluid may be supplied to one of the fluid passageways and drawn from other fluid passageway to ensure flow of fluid within the device.

Advantageously, the exchange aperture is an opening in the casing, preferably formed by removing, such as by cutting, an area of the casing. In an alternative embodiment, the exchange aperture is a porous area, preferably formed by treating the casing to render a portion of the casing porous.

In a preferred embodiment, more than one exchange aperture exposes the same fluid passageway.

In one embodiment, the porous portions of the more than one exchange aperture have different porosities. The porosity of each porous portion will depend upon the intended function of the specific porous portion.

In a preferred embodiment having two or more of fluid passageways or two or more porous portions on one fluid passageway, the porous portions have different porosities from one another. The use of porous portions and/or fluid passageways having different porosities enables different selections of molecular exchange at different exchange apertures along the casing.

For example, when the device is being used to deliver a drug into the bloodstream of a subject and monitor the concentration of the drug in the bloodstream, at least one porous portion will require a porosity that enables the drug to pass through the porous area into the bloodstream and at least one porous portion that has a porosity allowing the drug bound to a carrier, such as a plasma protein, for example albumin, to pass through the hollow area into the respective fluid passageway. The latter porous portion, located further downstream to other porous portion with respect to the flow of fluid within the at least two fluid passageways, will need to have a porosity that allows the passage of larger particles, i.e. the drug bound to a carrier as opposed to the drug alone. A skilled person will appreciate that the desired porosity of the porous portion of a fluid passageway will depend upon the size of the molecule that is intended to be exchanged across the porous portion adjacent to the exchange aperture. This arrangement will enable both the free (unbound to carrier) concentration and the total (unbound and bound to carrier) concentration of the drug to be determined.

In a preferred embodiment, the at least two fluid passageways have aligned exchange apertures. In use, an exchange aperture may rest against the internal walls of the vessel preventing access to the porous portion of the fluid passageway adjacent to the exchange aperture, as it is often the case that the device is not inserted into centre of the vessel. By providing aligned exchange apertures, it is more likely that at least one of the exchange apertures will be in contact with the flow of fluid within the vessel.

Alternatively, the exchange apertures may be positioned along the respective fluid passageway so that the apertures are not aligned. Such an arrangement is advantageous when the exchange apertures are intended to be used for different purposes.

In a preferred embodiment, the casing supports the at least two fluid passageways in the form of a tube, which are separated by the central separator along the length of the exchange aperture. The separator provides support to the tubing, whilst enabling a substantially large extent of exposure to the fluid passageway. In such an embodiment exchange of molecules may occur over substantially the entire circumference of the exposed tube, thereby providing a maximum surface area and increasing the efficiency of the exchange of molecules.

In a preferred embodiment of the invention, the at least two fluid passageways are held away from the separator in the porous section as a consequence of the hollow tubes being sealed where they enter and exit the porous section, thereby enabling substantially 100% of the circumference of the porous portion of the fluid passageway to be exposed. This provides the advantage of maximising the surface area of the porous region in contact with the environment external to the device. Preferably, the at least two fluid passageways are sealed by glue.

Advantageously, the distal end of the device comprises a plug in the end of the casing. More advantageously in this embodiment, the separator extends to the distal end of the casing and contains a fluid aperture to allow flow from one of the fluid passageway to another fluid passageway.

Alternatively, the distal end of the casing is formed as a tip containing a flow chamber to allow flow from the end of at least one of the fluid passageways into the end of another fluid passageway. Advantageously, the ends of the fluid passageways are within the flow chamber, such that any bond between the end of the fluid passageway and the distal end of the casing is remote from the exchange aperture to avoid fragmentation of the tube/porous membrane attached to the inside of the casing.

Preferably, the flow chamber has a sensor arrangement for detecting a (e.g., sensors 20, FIG. 3). For example, the sensor arrangement is a fibre optic and a reflector, wherein the fibre optic and reflector are positioned at the distal end of the device to enable spectrological measurements, for example, spectrophotometric measurement. Alternatively the sensor is a wave guide, conductor, photoelectric, electro-active or electrochemical sensor.

Advantageously, the molecular exchange device further comprises a channel leading from the proximal end of the casing to the distal end of the casing to provide additional materials to the interior and/or exterior of the distal end of the casing. Preferably, the channel is integral with the separator. More preferably, the channel is formed within the central axis of the separator.

The channel may supply fluid through to the distal end of the casing, in particular, into the flow chamber. In such an embodiment, the fluid can then pass into one or more of the fluid passageways. Of course, the reverse is possible, with fluids being passed along the fluid passageways into the distal end of the casing and then drawn out through the channel to the proximal end of the casing.

In an advantageous embodiment, the channel delivers a composition to activate a particular drug being administered by the device.

The channel may also be used to receive an additional component. For example, a guide wire may be inserted for positioning the molecular exchange device into the desired position within a subject. Advantageously, a probe (e.g., probe 28, FIG. 7) may be provided within the channel, such as electrical, sonic or optical probes, that may be used for detection and/or analysis. In a preferred embodiment, the channel may be exposed to the environment external to the device, to enable such a probe to have direct contact with the external environment. For example, a fibre optic or light source could be provided at the distal end of the molecular exchange device to allow guidance of the device during insertion into a subject.

Preferably, the proximal end of the casing is adapted for attachment to a catheter or cannular (catheter or cannular 26, FIG. 1), to accommodate insertion of the molecular exchange device into the subject. Insertion of the device using a catheter or cannular is a minimally invasive procedure.

More preferably, the proximal end of the casing is a lockable-mating arrangement or anchoring member (e.g., anchoring member 15, FIGS. 1 and 15) for connecting to an invasive port (e.g., port 24, FIG 1). In a medical application, it is possible that the subject will already have an existing invasive port inserted. Therefore, preferably, the proximal end is a lockable-mating arrangement or anchoring member for connecting to an existing invasive port, which reduces damage caused by insertion of the molecular exchange device into the subject.

More preferably, the proximal end of the casing is adapted for attachment to a pump (e.g., pump 22, FIG. 15). The pump allows fluid to be pumped into the fluid passageways and/or drawn from the fluid passageways, to ensure flow of the fluid through the device. Fluid may flow in both directions through the fluid passageways of the device. The intended use of the individual fluid passageway will determine whether the pump provides fluid flow through the fluid passageway in one direction or both directions. As will be appreciated, when the device has two or more of fluid passageways, the supply to and/or return of fluid from each of the fluid passageways will depend upon its required function.

Advantageously, the proximal end of the casing is adapted for attachment to an external device. More advantageously, the proximal end of the casing is adapted for attachment to two or more of external devices. The one or more external devices may be attached directly to the ends of the fluid passageways at the proximal ends of the device or indirectly attached to the fluid passageways via connecting tubing.

In a preferred embodiment, the external devices analyse the composition of the fluid drawn from one or more of the fluid passageways. Advantageously, the external device determines the presence of one or more molecules in the fluid from the fluid passageways and/or measures the amount/concentration of one or more molecules in the fluid. More advantageously, the external devices control delivery of a drug into the patient through the molecular exchange device.

In an advantageous embodiment, the device can provide a self-maintaining mechanism for drug delivery, to maintain the concentration of the drug at a predetermined level.

The present invention further provides a system for controlling the concentration of a first substance in a fluid passageway of the molecular exchange device. The system comprises a molecular exchange device, a control device linked to the molecular exchange device, wherein the control device measures the concentration of a second substance in a fluid passageway and controls the supply of the first substance into a fluid passageway, preferably in response to the measured concentration. This will subsequently maintain the concentration of the composition in the environment external to the molecular exchange device. The first and second substances may be the same or different from one another.

In accordance with a further aspect of the present invention, there is provided a method of manufacturing a molecular exchange device, the method comprising the steps of:
i) forming of a casing
ii) providing at least two fluid passageways within the casing
iii) forming of at least one exchange aperture in the casing Advantageously, steps i), ii) and/or iii) occur simultaneously. For example, the casing may be formed by an extrusion process that provides the at least two fluid passageways and/or the at least one exchange aperture during the forming of the casing.

Advantageously, the method further comprising the step of forming a separator to separate the at least two fluid passageways.

Preferably, the casing is formed by moulding. More preferably, at least one exchange aperture is formed by the moulding of the casing. Advantageously, the casing is formed through an extrusion process. More advantageously, the exchange aperture is formed by cutting away a portion of the casing. Alternatively, the exchange aperture is formed in the opening during the manufacture of the casing, for example during an extrusion process. In an alternative embodiment, the exchange aperture is a porous area, preferably formed by treating the casing to render a portion of the casing porous. The casing may be treated during and/or post formation of the casing. The treatment may be by laser, such as laser ablation, x-ray, spark erosion, etching, oxidation, use of salt treatment during an extrusion process, or other microfabrication processes to allow transfer of molecules from the inside of the fluid passageway to the environment external to the device and vice versa.

In a preferred embodiment at the least two fluid passageways are inserted into the casing after the forming of the exchange apertures. More preferably, the fluid passageways are inserted into the casing after the sealing of the distal end of the casing. Advantageously, the fluid passageways have a shaped cross section to ensure insertion into the casing in the correct orientation. More advantageously, the fluid passageway has a circular or non-circular shaped cross section for orientation into the lumen. In a preferred embodiment the cross section of the fluid passageway has at least one straight edge. More preferably, the cross section of the fluid passageway is D-shaped.

In a preferred embodiment the distal end of the casing is formed sealed as part of the moulding process. Alternatively, the method further comprises the step of sealing the distal end of the casing. Advantageously, the distal end of the casing is sealed by any method that causes the molecules of the distal end to flow together, such as heat sealing, cold sealing or crimping.

In order that the present invention may be more readily understood, non limiting embodiments thereof will now be described, by way of example, with reference to the accompanying drawings in which.

Figure 1:
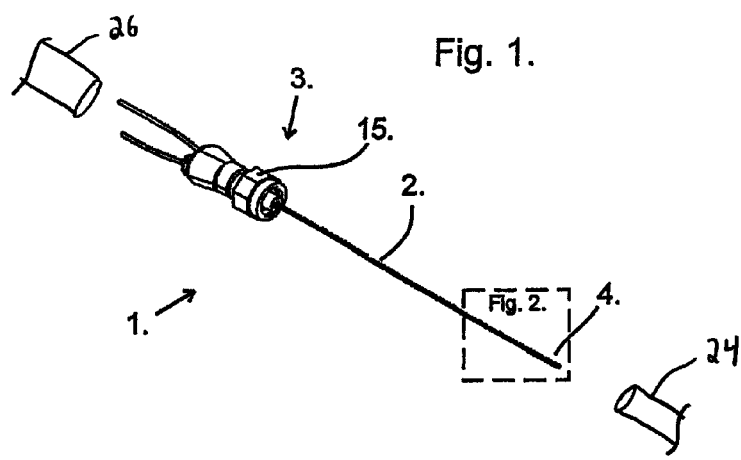
FIG. 1 is an overall illustration of a first embodiment of a molecular exchange device in accordance with the present invention and an anchoring unit to hold the device in position during use.

As illustrated in FIG. 1, there is a first embodiment of a molecular exchange device (1) according to the present invention comprises a casing (2) made of HDPE, extending from a proximal end (3) to a distal end (4); and an anchoring unit (15) to hold the device (1) in position during use.

Figure 2:
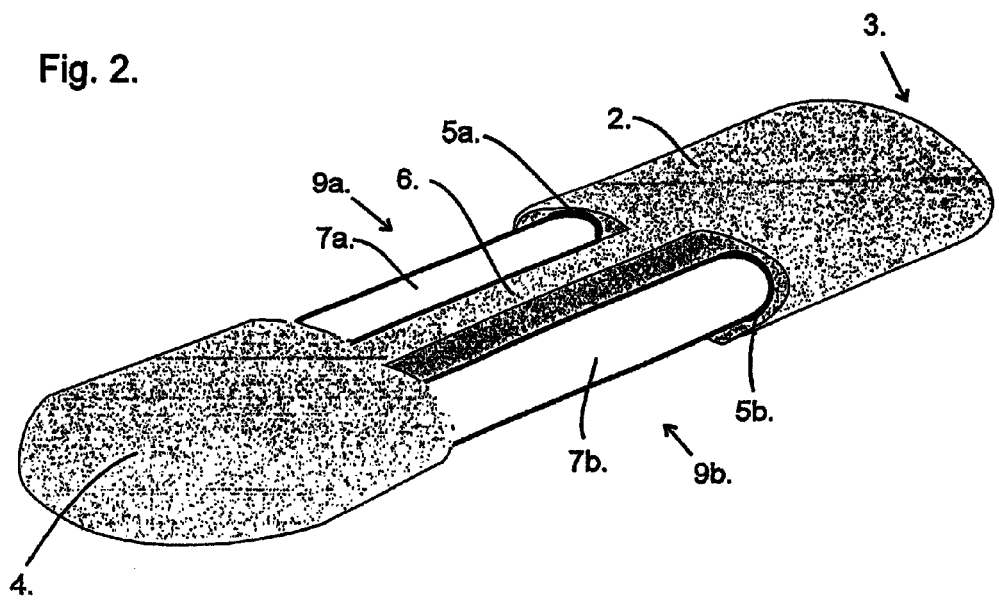
FIG. 2 is an enlarged view of a distal portion of the first embodiment of a molecular exchange device in accordance with the present invention.

As shown in more detail, FIG. 2, the casing (2) supports two fluid passageways (7a, 7b) extending from the proximal end (3) to the distal end (4); a separator (6) extending along the length of the casing (2) separating the two fluid passageways; two aligned exchange apertures, between the proximal end (3) and the distal end (4) of the casing, exposing the fluid passageways (7a, 7b). The portion of the fluid passageways (7a, 7b) exposed by the opposed exchange apertures are porous.

In this embodiment, the casing (2) defines two internal lumens (5a, 5b) that extend within the casing from the proximal end (3) to the distal end (4). A separator (6), integral with the casing (2), extends along the central axis of the casing (2) defining the two lumens (5a, 5b) within the casing (2). It is also envisaged that the separator (6) is not integral with the casing (2), but firmly attached thereto.

In this embodiment, the lumens (5a, 5b) each hold a fluid passageway (7a, 7b) in the form of a tube. The tubes (7a, 7b) are suitable for fluid to travel within the passageway. The fluid may be supplied or drawn at the proximal end (3) of the tube (7a, 7b). The tubes are formed from a porous membrane that allows the selective exchange of molecules in one or both directions across the membrane. The level of porosity of the porous membrane will depend upon the intended use of the molecular exchange device (1). The tubes (7a, 7b) have a porosity that enables a specific molecule or composition to cross the membrane from the environment external to the tube (7a, 7b) into the tube (7a, 7b) and vice versa, for a particular use of the molecular exchange device (1).

Figure 3:
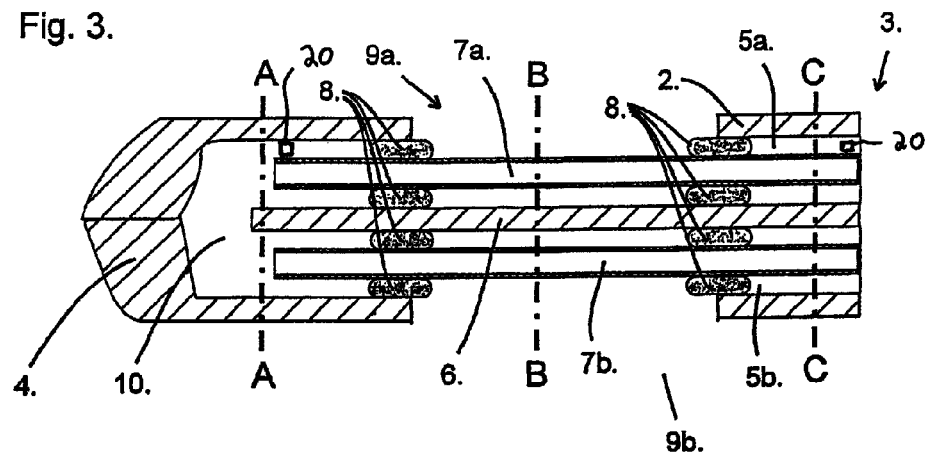
FIG. 3 is a cut away plan view of the first embodiment of a molecular exchange device in accordance with the present invention.
Figure 4:
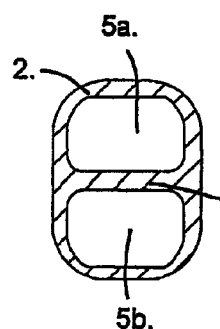
FIG. 4 is a cross-sectional view of the first embodiment of a molecular exchange device sectioned through AA.
Figure 5:
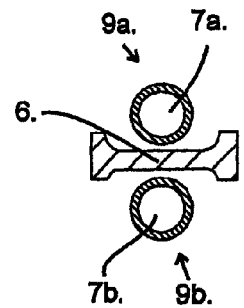
FIG. 5 is a cross-sectional view of the first embodiment of a molecular exchange device sectional through BB.
Figure 6:
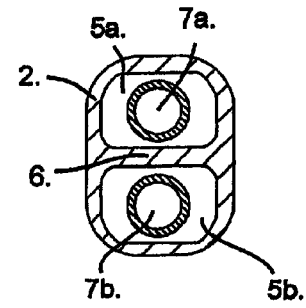
FIG. 6 is a cross-sectional view of the first embodiment of a molecular exchange device sectioned through CC.

As shown in FIGS. 2 and 3, the casing (2) has aligning exchange apertures (9a, 9b) that each expose a tube (7a, 7b). It is also envisaged that the apertures (9a, 9b) are not aligned along the length of the casing (2). In this embodiment the entire circumference of the tube (7a, 7b) adjacent to the exchange aperture (9a, 9b) is exposed to the external environment, as shown in FIG. 5. The tube (7a, 7b) is sealed to the casing (2) by, for example, glue and this arrangement holds the tube away from the surface of the separator (6), such that 100% or substantially 100% of the circumference of the tube (7a, 7b), including that adjacent to the exchange aperture, is exposed to the external environment.

In this embodiment and as shown in FIG. 3, the distal end (4) of the casing (2) containing a flow chamber (10) that permits the passage of a fluid from one of the tubes (7a) to the other tube (7b). It is envisaged that fluid may flow in either direction in each tube (7a, 7b) and, as such, the flow chamber (10) permits the passage of fluid in both directions, i.e. from one tube (7a) to the other tube (7b) and vice versa. As illustrated in FIG. 2, the external configuration of the flow chamber (10) is tapered, to allow easy insertion of the molecular exchange device (1) into a subject.

As shown in more detail in FIG. 3, the tubes (7a, 7b) extend into and terminate within the flow chamber (10). The tubes (7a, 7b) are sealed into the casing by, for example, heat treatment or glue, such as UV curing glue, cyanoacrylate, two-part epoxy resin and any other appropriate method, including mechanical means. In this embodiment the molecular exchange device (1), as shown in FIG. 7, is further provided with a channel (11), extending from the proximal end (3) to the distal end (4) of the casing (2), that runs internally through separator (6).

Figure 7:
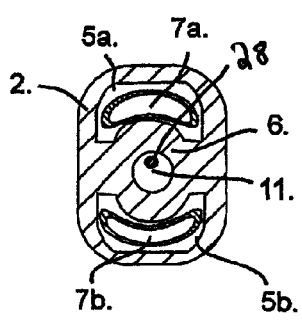
FIG. 7 is a cross-sectional view of a second embodiment of an molecular exchange device in accordance with the present invention.

In this embodiment, as shown in FIG. 7, the tubes (7a, 7b) are profiled to accommodate the channel (11). The profile of the tubes (7a, 7b) allow the correct orientation of the tubes (7a, 7b) in the lumens (5a, 5b).

The channel (11) provides a means to transport materials, such as a drug, into and out of the flow chamber, once the molecular exchange device (1) has been placed in the desired position within a subject.

In this embodiment, a sensor 20 (FIG. 3) may be positioned on one or both of the ends of the tubes (7a, 7b), the sensor measuring, for example, a drug within the flow chamber (10). The rate of delivery of the drug into the device (1) can be altered in accordance with the concentration of the drug across the membrane. The rate of delivery of the drug can be controlled by changing the quantity of a drug introduced into the device. The higher the quantity of a drug passed into the device (1), the greater the delivery of the drug to the environment external to the device (1) when a concentration gradient that has been set up across the dialysis membrane.

As illustrated in FIG. 3, in use, fluid may be passed into one of the tubes (7a, 7b) of the molecular exchange device (1). The fluid may be passed along the tube (7a), into the flow chamber, into the second tube (7b), along the second tube (7b) to the opening of the passageway at the proximal end (3) of the device (1). Due to the nature of the material of the casing (1), the fluid and any compositions in it will be maintained within the tube (7), except at the exchange apertures. At each of the exchange apertures in the respective lumens (5a, 5b) of the casing (2), the fluid carried in the respective tube (7a, 7b) will be exposed to the environment surrounding the molecular exchange device (1). Depending on various factors, such as the relative internal and external concentration of molecules/compositions, the specific porosity of the porous area of the tube (7a, 7b) and the intended use of the molecular exchange device (1), molecules/compositions present in the tube (7a, 7b) may be supplied across the porous membrane into the environment external to the device (1) or molecules/compositions present in the external environment may be drawn across the porous membrane are into the tube (7a, 7b).

The first tube (7a) may have the same properties (for example porosity) as the other tube (7b) and used for the same function. Alternatively, the first tube (7a) could be used to supply and/or absorb different molecules/compositions and, as such, have different properties.

Figure 8:
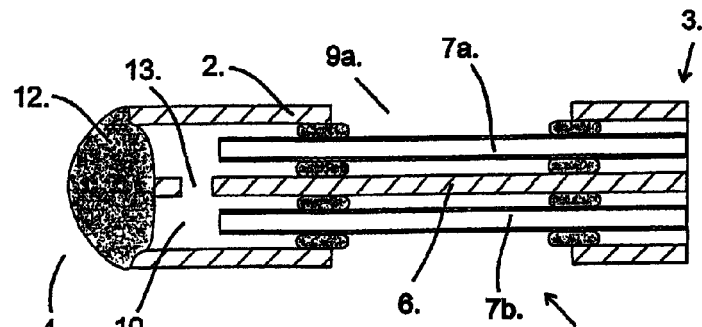
FIG. 8 is a cut-away view of an alternative embodiment of a molecular exchange device in accordance with the present invention.

As illustrated in FIG. 8, the distal end (4) of the casing (2) may alternatively comprise a plug (12). To permit flow between the tubes (7a, 7b), the separator (6) has a flow aperture (13) to allow flow from one tube (7a) to the other tube (7b) and vice versa.

Figure 9:
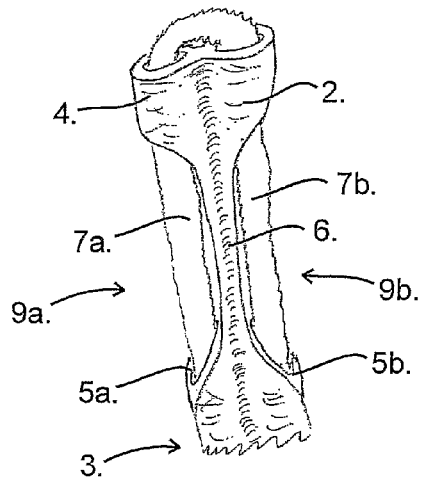
FIG. 9 is alternative embodiment of a molecular exchange device in accordance with the present invention.

As illustrated in FIG. 9, a further embodiment of the present invention comprises a casing (2) having an integral separator (6), extending from the proximal end (3) to the distal end (4) of the casing (2). A fluid passageway in the form of a tube extends within one of the lumens (5a) from the proximal end (3) to the distal end (4) of the casing, extending beyond the distal end of the casing, bends back on itself, and extends back into the second lumen (5b) from the distal end (4) to the proximal end (3) of the casing (2), providing a single uninterrupted tube (7a, 7b), anchored, at least, at the proximal end (3) of the casing (2). Therefore, fragmentation of the tubes (7a, 7b), in use, is prevented. The tube may also be bonded along the length of the casing (2) but only to retain its orientation rather than provide additional bonding.

A further embodiment of the invention (not shown), is the same as that described with reference to FIG. 9 above, except that the tube at the distal end (4) of the casing is fully contained within the casing (2); the casing being in a similar confirmation as shown in FIGS. 2 and 3.

In use, the fluid may be passed along the first passageway (7a), through the distal end and along the second passageway (7b) to the opening of the passageway at the proximal end of the device (1). Again the fluid is exposed to the external environment at each exchange apertures along the casing, permitting selective exchange of molecules/compositions across the porous portion of the tubes (7a, 7b).

Figure 10:
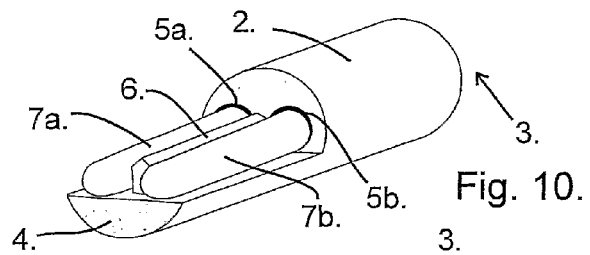
FIG. 10 is an alternative embodiment of a molecular exchange device in accordance with the present invention.
Figure 15:
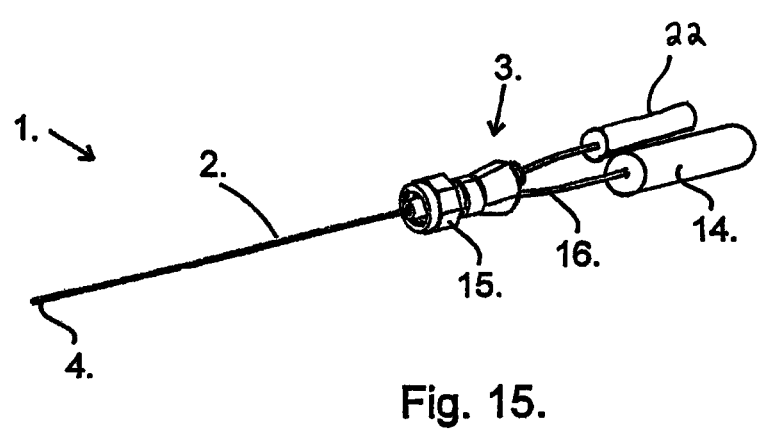
FIG. 15 is an embodiment of an apparatus in accordance with the present invention.

As shown in FIG. 10, the two tubes (7a, 7b) are arranged in two distinct lumens (5a, 5b). Each of the tubes (7a, 7b) has a concentric arrangement within the tube, such that fluid may flow along a internal tube and back along the external tube and vice versa. There is no fluid connection between the two fluid passageways (7a, 7b). Such an arrangement is suitable, for example, for use when one of the tubes (7a) provides a dialysis membrane and the other tube (7b) monitors the concentration levels of molecules/compositions in the external environment. With regard to the latter, molecule/compositions cross the porous portion of the tube (7b) from the external environment into the tube (7b) of the device (1), and travel along the tube (7b) to the proximal end (3) of the casing (2) and carried to an external device (14) for analysis, as shown in FIG. 15.

Figure 11:
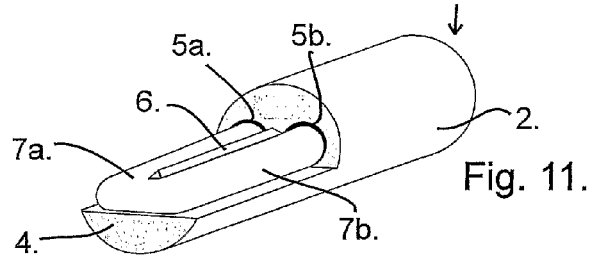
FIG. 11 is an alternative embodiment of a molecular exchange device in accordance with the present invention.

Alternatively, as shown in FIG. 11, one tube provides two fluid passageways (7a, 7b).

Figure 12:
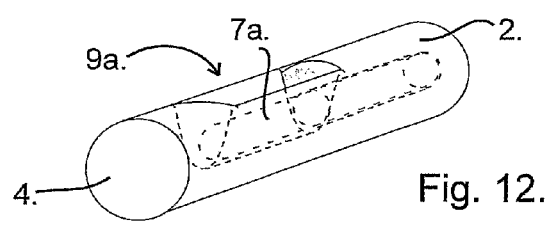
FIG. 12 is an alternative embodiment of a molecular exchange device in accordance with the present invention.
Figure 16:
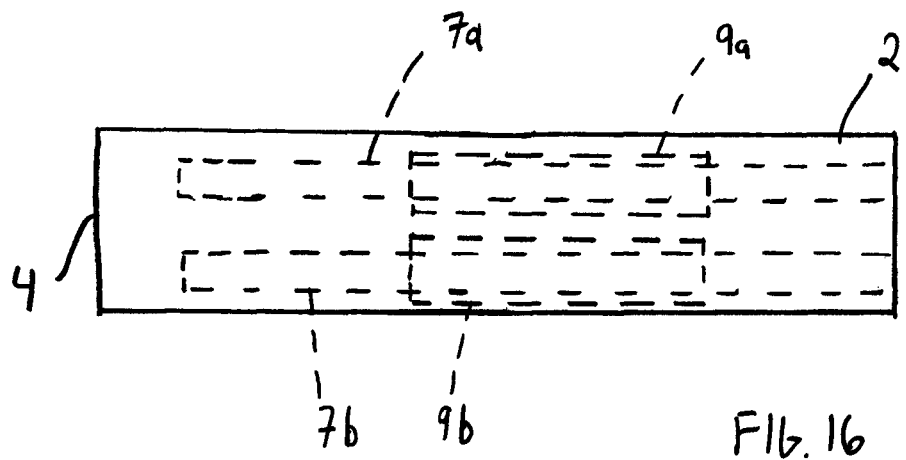
FIG. 16 is an alternative embodiment of a molecular exchange device in accordance with the present invention.
Figure 17:
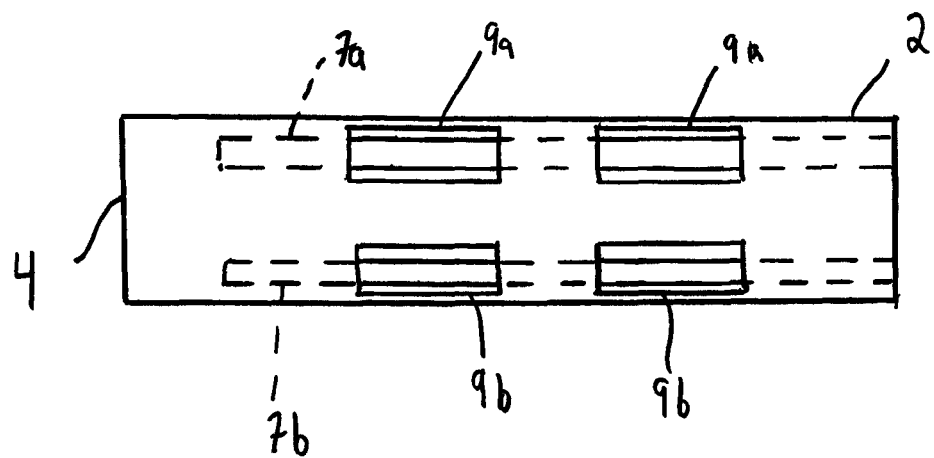
FIG. 17 is an alternative embodiment of a molecular exchange device in accordance with the present invention.

A further embodiment of the invention, as shown in FIG. 12, comprises a device (1) in which the external walls of the casing (2) are arranged at the exchange aperture (9) to form a concave aperture (9a). FIG. 16 shows another embodiment of a device (1) in which the exchange apertures (9a, 9b) comprises porous portions of the casing (2). FIG. 17 shows another embodiment of a device (1) in which there are two exchange apertures (9a, 9b) that exposes the same fluid passageway (7a, 7b).

Figure 13:
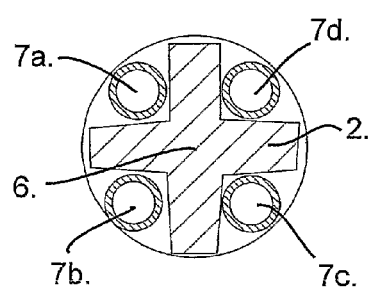
FIG. 13 is a cross-sectional view of an alternative embodiment of a molecular exchange device in accordance with the present invention.
Figure 14:
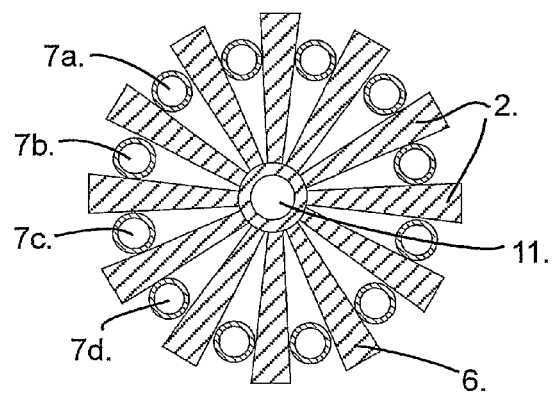
FIG. 14 is a cross-sectional view of an alternative embodiment of a molecular exchange device in accordance with the present invention.

As shown in FIGS. 13 and 14, it is envisaged that a molecular exchange device (1) according to the present invention can be provided with a casing (2) having two or more of fluid passageways (7a, 7b, 7c, 7d), separated by a separator (6). This permits multiple molecular exchange to be carrying out using one device. For example, the molecular exchange may be for analysis, dialysis, delivery etc. As shown in FIG. 13, the device (1) has four fluid passageways (7a, 7b, 7c, 7d). Alternatively, as shown in FIG. 14, the device (1) has twelve fluid passageways (7a, 7b, 7c, 7d etc.)

FIG. 15 illustrates schematically an apparatus embodying the present invention. A molecular exchange device (1) is connected with an anchoring unit (15), such as a luer lock, and is in fluid communication, by means of tubing (16), with an external device (14). The external device (14) may analyse fluid received from the device (1), for instance to detect certain molecules/compositions or concentrations of molecule/compositions, or may supply molecule/compositions in a fluid for supply to the device (1), for instance maintaining concentrations of those compositions in the fluid passageways.

A molecular exchange device (1) according to the present invention is preferably manufactured by injection moulding the casing (2) having a central separator (6) and plurality of exchange apertures (9) and then heat-sealing or crimping the distal end (4), either before or after insertion of the hollow tubes (7). However, other methods of manufacture known to those of skill in the art are also possible. For instance, the casing (2) could be formed as an extrusion process, with the walls of the casing (2) being removed to form the exchange apertures (9). Alternatively, the exchange apertures could be formed by treating the material of the casing (2) appropriately, as would be appreciated by those of skill in the art, to render the wall of the casing porous.

The molecular exchange device of the present invention and one or more external devices can be used to analyse, measure or deliver industrial, chemical, fermentation and animal or plant compositions. The molecular exchange device may be used in industrial, chemical or fermentation processes and the human or animal body.

The molecular exchange advice according to the present invention is intended to be used in the human or animal bodies including but not restricted to the circulatory system, insertion into blood vessels, lymphatic system, muscles, ear, mouth, tissue fat and internal organs.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A molecular exchange device comprising:
   a casing, extending from a proximal end portion to a distal end portion, supporting at least two fluid conduits extending from the proximal end portion to the distal end portion;
   the at least two fluid conduits comprising a first fluid conduit and a second fluid conduit, the first fluid conduit comprising a lumen allowing fluid flow in a first direction from the proximal end portion to the distal end portion of the casing, the second fluid conduit comprising a lumen allowing fluid flow in a second direction, opposite the first direction, from the distal end portion to the proximal end portion of the casing;
   the casing comprising at least first and second exchange apertures located between the distal end portion and the proximal end portion, wherein the first fluid conduit comprises a porous portion exposed by the first exchange aperture, and the second fluid conduit comprises a porous portion exposed by the second exchange aperture;

wherein the proximal end portion of the casing is configured to house a proximal end portion of the first fluid conduit and a proximal end portion of the second fluid conduit, and the distal end portion of the casing is configured to house a distal end portion of the first fluid conduit and a distal end portion of the second fluid conduit such that the proximal end portions of the first and second fluid conduits are supported by the casing proximal end portion and the distal end portions of the first and second fluid conduits are supported by the casing distal end portion; and a separator extending from the proximal end portion of the casing to the distal end portion of the casing, the first and second fluid conduits being arranged on opposite sides of the separator;

wherein the first fluid conduit is spaced from the separator within the first exchange aperture to define a gap between the first fluid conduit and the separator, the gap allowing the porous portion of the first fluid conduit to be exposed to an external fluid around the entire circumference of the porous portion of the first fluid conduit;

wherein the second fluid conduit is spaced from the separator within the second exchange aperture to define a gap between the second fluid conduit and the separator, the gap allowing the porous portion of the second fluid conduit to be exposed to an external fluid around the entire circumference of the porous portion of the second fluid conduit.

2. The molecular exchange device according to claim 1, wherein the separator extends along a central axis of the casing.

3. The molecular exchange device according to claim 1, wherein the porous portion of first fluid conduit comprises a porous membrane bonded with the casing at the proximal and distal ends of the first exchange aperture and the porous portion of the second fluid conduit comprises a porous membrane bonded with the casing at the proximal and distal ends of the second exchange aperture.

4. The molecular exchange device according to claim 3, wherein each porous membrane comprises a dialysis membrane.

5. The molecular exchange device according to claim 1, wherein the first and second fluid conduits are defined by at least one tube that extends from the proximal end portion to the distal end portion of the casing, folds back on itself at the distal end portion and extends from the distal end portion to the proximal end portion of the casing, providing the first and second fluid conduits.

6. The molecular exchange device according to claim 1, wherein each of the first and second fluid conduits has a circular or non-circular shaped cross section or the cross section has one straight edge and or the cross section is D-shaped.

7. The molecular exchange device according to claim 1, wherein each of the first and second exchange apertures is an opening, formed by (a) a cut-away a portion of the casing; or (b) a porous portion of the casing.

8. The molecular exchange device according to claim 1, wherein more than one exchange aperture exposes the same fluid conduit.

9. The molecular exchange device according to claim 8, wherein the fluid conduit exposed to more than one exchange aperture comprises multiple porous portions having different porosities.

10. The molecular exchange device according to claim 1, wherein the first and second exchange apertures comprise aligned or non- aligned exchange apertures.

11. The molecular exchange device according to claim 1, further comprising a plug in the distal end portion of the casing.

12. The molecular exchange device according to claim 1, wherein the separator extends into the distal end portion of the casing and contains a fluid aperture to allow flow from the first fluid conduit to the second fluid conduit.

13. The molecular exchange device according to claim 1, wherein the distal end portion of the casing is formed as a non-porous tip containing a flow chamber to allow flow from one end of the first fluid conduit into the end of the second fluid conduit.

14. The molecular exchange device according to claim 13, wherein the end of at least one of the fluid conduits extends into the flow chamber.

15. The molecular exchange device according to claim 13, wherein the flow chamber has a sensor arrangement to enable spectrologic measurement.

16. The molecular exchange device according to claim 15, wherein the spectrologic measurement is spectrophotometric measurement.

17. The molecular exchange device according to claim 15, wherein the sensor arrangement is a reflector, wave guide, conductor, photoelectric, electro-active or electrochemical sensor.

18. The molecular exchange device according to claim 1, further comprising a channel extending through the casing from the proximal end portion of the casing to the distal end portion of the casing, the channel providing access for additional materials to the interior and/or exterior of the distal end of the casing.

19. The molecular exchange device according to claim 18, wherein the channel is integral with the separator.

20. The molecular exchange device according to claim 19, wherein the channel is formed along the central axis of the separator.

21. The molecular exchange device according to claim 18, wherein the channel provides access to or access for an optical, sonic and/or electrical probe.

22. The molecular exchange device according to claim 1, wherein the proximal end portion of the casing is adapted for attachment to a catheter and/or cannular.

23. The molecular exchange device according to claim 1, wherein the proximal end portion of the casing is a lockable-mating arrangement and/or anchoring member for connecting to an invasive port.

24. The molecular exchange device according to claim 1, wherein the proximal end portion of the casing is adapted for attachment to a pump.

25. The molecular exchange device according to claim 1, wherein the proximal end portion of the casing is adapted for attachment to an external device.

26. The molecular exchange device according to claim 1, wherein the distal end portion of the casing comprises a non-porous outer wall completely surrounding the distal end portions of the first and second fluid conduits.

27. The molecular exchange device according to claim 1, wherein the distal end portion of the casing is non-porous and comprises first and second openings on opposite sides of the separator, the first fluid conduit extending through the first opening into the casing distal end portion such that the entire distal end portion of the first fluid conduit is housed within the casing distal end portion, the second fluid conduit extending through the second opening into the casing distal end portion such that the entire distal end portion of the second fluid conduit is housed within the casing distal end portion.

28. The molecular exchange device according to claim 27, wherein the proximal end portion of the casing is non-porous and comprises third and fourth openings on opposite sides of the separator, the first fluid conduit extending through the third opening into the casing proximal end portion such that the entire proximal end portion of the first fluid conduit is housed within the casing proximal end portion, the second fluid conduit extending through the fourth opening into the casing proximal end portion such that the entire proximal end portion of the second fluid conduit is housed within the casing proximal end portion.

29. The molecular exchange device according to claim 28, wherein the separator is integral with the casing distal end portion and the casing proximal end portion.

30. The molecular exchange device according to claim 27, further comprising a seal between the distal end portion of the first fluid conduit and the casing distal end portion within the first opening and another seal between the distal end portion of the second fluid conduit and the casing distal end portion within the second opening.

31. The molecular exchange device according to claim 28, further comprising a seal between the proximal end portion of the first fluid conduit and the casing proximal end portion within the third opening and another seal between the proximal end portion of the second fluid conduit and the casing proximal end portion within the fourth opening.

32. A method of manufacturing a molecular exchange device, wherein the method comprises the steps of:
   i) forming of a casing comprising a proximal end portion and a distal end portion;
   ii) providing at least two fluid conduits, the at least two fluid conduits comprising a first fluid conduit and a second fluid conduit, the first fluid conduit comprising a lumen allowing fluid flow in a first direction from the proximal end portion to the distal end portion of the casing, the second fluid conduit comprising a lumen allowing fluid flow in a second direction, opposite the first direction, from the distal end portion to the proximal end portion of the casing;
   iii) forming of at least first and second exchange apertures in the casing between the distal end portion and the proximal end portion, wherein the first fluid conduit comprises a porous portion exposed by the first exchange aperture, and the second fluid conduit comprises a porous portion exposed by the second exchange aperture;
   wherein the proximal end portion of the casing is configured to house a proximal end portion of the first fluid conduit and a proximal end portion of the second fluid conduit, and the distal end portion of the casing is configured to house a distal end portion of the first fluid conduit and a distal end portion of the second fluid conduit such that the proximal end portions of the first and second fluid conduits are supported by the casing proximal end portion and the distal end portions of the first and second fluid conduits are supported by the casing distal end portion; and
   iv) providing a separator extending from the proximal end portion of the casing to the distal end portion of the casing, the first and second fluid conduits being arranged on opposite sides of the separator;
   wherein the first fluid conduit is spaced from the separator within the first exchange aperture to define a gap between the first fluid conduit and the separator, the gap allowing the porous portion of the first fluid conduit to be exposed to an external fluid around the entire circumference of the porous portion of the first fluid conduit;
   wherein the second fluid conduit is spaced from the separator within the second exchange aperture to define a gap between the second fluid conduit and the separator, the gap allowing the porous portion of the second fluid conduit to be exposed to an external fluid around the entire circumference of the porous portion of the second fluid conduit.

33. The method according to claim 32, wherein steps i), ii) and/or iii) occur simultaneously.

34. The method according to claim 32, wherein the casing is formed by moulding.

35. The method according to claim 34, wherein the first and second exchange apertures are formed by the moulding of the casing.

36. The method according to claim 32, wherein the exchange apertures are formed by treating the casing by laser ablation, x-ray, such spark erosion, etching, or oxidation use of salt treatment during an extrusion process or other microfabrication processes, to render the casing porous.

37. The method according to claim 32, wherein the least two fluid conduits are inserted into the casing after forming the exchange apertures.

38. The method according to claim 32, wherein the at least two fluid conduits are inserted into casing after the sealing of the distal end of the casing.

39. The method according to claim 32, wherein at least one of the fluid conduits has a cross-section which is circular or non-circular having one straight edge or is D-shaped, for orientation into the lumen.

40. The method according to claim 32, wherein the distal end of the casing is sealed.

41. The method according to claim 40, wherein the distal end of the casing is sealed by heat sealing, cold sealing, crimping or mechanical methods.

* * * * *